United States Patent
Rangarajan et al.

(10) Patent No.: US 6,617,087 B1
(45) Date of Patent: Sep. 9, 2003

(54) USE OF SCATTEROMETRY TO MEASURE PATTERN ACCURACY

(75) Inventors: Bharath Rangarajan, Santa Clara, CA (US); Bhanwar Singh, Morgan Hill, CA (US); Ramkumar Subramanian, San Jose, CA (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 0 days.

(21) Appl. No.: 09/893,272

(22) Filed: Jun. 27, 2001

(51) Int. Cl.[7] .............................. G03C 5/00; G01N 21/00

(52) U.S. Cl. ........................ 430/30; 430/329; 356/237.2

(58) Field of Search ............................... 356/237.2, 445, 356/446; 430/30, 329, 5; 438/401, 780, 5, 7, 14, 16; 355/53, 55; 382/145

(56) References Cited

U.S. PATENT DOCUMENTS

| | | | | |
|---|---|---|---|---|
| 4,586,822 A | * | 5/1986 | Tanimoto | 356/394 |
| 4,751,169 A | * | 6/1988 | Behringer et al. | 430/296 |
| 4,952,058 A | * | 8/1990 | Noguchi et al. | 356/237.5 |
| 5,123,743 A | * | 6/1992 | Feldman | 356/394 |
| 5,343,293 A | | 8/1994 | Berger et al. | |
| 5,402,224 A | * | 3/1995 | Hirukawa et al. | 356/124 |
| 5,667,918 A | * | 9/1997 | Brainerd et al. | 430/5 |
| 5,811,223 A | * | 9/1998 | Bae | 430/312 |
| 5,849,440 A | * | 12/1998 | Lucas et al. | 430/5 |
| 5,880,838 A | | 3/1999 | Marx et al. | |
| 6,052,188 A | | 4/2000 | Fluckiger et al. | |
| 6,104,486 A | | 8/2000 | Arimoto | |
| 6,130,016 A | * | 10/2000 | Kent | 430/30 |
| 6,245,584 B1 | * | 6/2001 | Marinaro et al. | 438/14 |
| 6,383,824 B1 | * | 5/2002 | Lensing | 438/14 |
| 6,426,168 B1 | * | 7/2002 | Johnson | 430/30 |
| 6,433,878 B1 | * | 8/2002 | Niu et al. | 356/603 |
| 6,479,200 B1 | * | 11/2002 | Stirton | 430/30 |
| 6,501,534 B1 | * | 12/2002 | Singh et al. | 355/55 |
| 6,513,151 B1 | * | 1/2003 | Erhardt et al. | 716/21 |
| 6,516,085 B1 | * | 2/2003 | Wiley et al. | 382/144 |
| 6,529,621 B1 | * | 3/2003 | Glasser et al. | 382/144 |

OTHER PUBLICATIONS

"Scatterometry for the Measurement of Metal Features", In Metrology, Inspection, and Process Control for Microlithography XIV, Christopher J. Raymond, Steve W. Farrer and Scott Sucher, Proceedings of SPIE, vol. 3998, Feb. (2000), pp. 135–145.

"Manufacturing Considerations for Implementation of Scatterometry for Process Monitoring", In Metrology, Inspection, and Process Control for Microlithography XIV, John Allgair, Dave Benoit, Rob Hershey and Lloyd C. Litt (Motorola); Ibrahim Abdulhalim, Bill Braymer, Michael Faeyrman, John C Robinson, Umar Whitney, Yiping Xu, Piotr Zalicki and Joel Seligson (Kla–Tencor Corp.). Proceedings of SPIE. vol. 3998, Feb. (2000), pp. 125–134.

(List continued on next page.)

*Primary Examiner*—Zandra V. Smith
*Assistant Examiner*—Gordon J Stock
(74) *Attorney, Agent, or Firm*—Eschweiler & Associates, LLC

(57) ABSTRACT

The present invention provides a system and process for controlling the application of patterned resist coatings in an integrated circuit manufacturing process that employs multiple reticle patterns. One aspect of the invention relates to obtaining scatterometry measurements from a patterned resist and using the measurements to determine whether the correct reticle pattern was employed in forming the patterned resist. According to another aspect of the invention, the reticles are provided with grating patterns in addition to reticle patterns, whereby when the reticles are printed, gratings are formed in the resist. The gratings can be used, with scatterometry, to identify the reticle pattern. The reticles can be configured so that the gratings form in a non-functional portion of a wafer, such as a portion along a score line. Where it is, determined that the correct reticle pattern was not used, corrective action can be taken such as stripping the resist and reprocessing the affected wafers.

7 Claims, 3 Drawing Sheets

OTHER PUBLICATIONS

"Phase Profilometry for the 193 nm Lithography Gate Stack", In Metrology, Inspection, and Process Control for Microlithography XIV, Nickhil Jakatdar, Xinhui Niu, Junwei Bao, Costas Spanos, Sanjay Yedur and Alain Deleporte, Proceedings of SPIE, vol. 3998, Feb. (2000), pp. 116–124.

"Lithographic Process Monitoring using Diffraction Measurements", Metrology, Inspection, and Process Control for Microlithography XIV, Emmanuel M. Drege and Dale M. Byrne, Proceedings of SPIE, vol. 3998, Feb. (2000), 12 pp.

"An Integrated System of Optical Metrology for Deep Sub–Micron Lithography", Xinhui Niu, A dissertation submitted in partial satisfaction of the requirements for the degree of Doctor of Philosphy in Engineering–Electrical Engineering and Computer Sciences in the Graduate Division of the University of California, Berkeley, Spring, 1999, 153 pp., Call #308t, 1999, 324.

* cited by examiner

USE OF SCATTEROMETRY TO MEASURE PATTERN ACCURACY

TECHNICAL FIELD OF THE INVENTION

The present invention relates generally to semiconductor device manufacturing and more particularly to a system and a method for controlling the selection of reticles in a process employing a plurality of reticle patterns.

BACKGROUND OF THE INVENTION

In the semiconductor industry, there is a continuing trend toward high device densities. To achieve these high device densities, small features on semiconductor wafers are required. These may include the width and spacing of interconnecting lines, spacing and diameter of contact holes, and surface geometry of corners and edges.

High resolution lithographic processes are used to achieve small features. In general, lithography refers to processes for pattern transfer between various media. In lithography for integrated circuit fabrication, a silicon slice, the wafer, is coated uniformly with a radiation-sensitive film, the resist. The film is selectively exposed with radiation (such as visible light, ultraviolet light, x-rays, or an electron beam) through an intervening master template, the mask or reticle (the terms mask and reticle are used interchangeably herein), forming a particular pattern. Exposed areas of the coating become either more or less soluble than the unexposed areas, depending on the type of coating, in a particular solvent developer. The more soluble areas are removed with the developer in a developing step while the less soluble areas remain on the silicon wafer, thus forming a patterned coating. The pattern of the coating corresponds to the image, or negative image, of the reticle and is used in further processing of the silicon wafer.

Over the course of a device manufacturing process, a large number of lithographic processes are commonly employed. Each lithographic process involves a different reticle pattern; the reticles used for such processing are generally kept in cases that are labeled, with a bar code for example and/or the reticles themselves may also be labeled. Automated apparatus may be used to assist in selecting the correct reticle for a particular process step. On occasion, nonetheless, an incorrect reticle is selected and the affected wafers (those wafers processed with the incorrect reticle) are lost as defects. Therefore, their remains an unsatisfied need for systems and methods that mitigate or eliminate problems associated with incorrect reticle selection.

SUMMARY OF THE INVENTION

The following presents a simplified summary of the invention in order to provide a basic understanding of some of its aspects. This summary is not an extensive overview of the invention and is intended neither to identify key or critical elements of the invention nor to delineate its scope. The primary purpose of this summary is to present some concepts of the invention in a simplified form as a prelude to the more detailed description that is presented later.

The present invention provides a system and process for controlling the application of patterned resist coatings in an integrated circuit manufacturing process that employs multiple reticle patterns. One aspect of the invention relates to obtaining scatterometry measurements from a patterned resist and using the measurements to determine whether the correct reticle pattern was employed in forming the patterned resist. According to another aspect of the invention, the reticles are provided with grating patterns in addition to reticle patterns, whereby when the reticles are printed, gratings are formed in the resist. The gratings are then used, with scatterometry, to identify the reticle pattern. The reticles can be configured so that the gratings form in a non-functional portion of a wafer, such as a portion along a score line. Where it is determined that the correct reticle pattern was not used, an indication of the determination is provided and corrective action can be taken such as stripping the resist and reprocessing the affected wafers.

Other advantages and novel features of the invention will become apparent from the following detailed description of the invention and the accompanying drawings. The detailed description and drawings provide exemplary aspects or embodiments of the invention. These exemplary aspects of embodiments are indicative of but a few of the various ways in which the principles of the invention can be employed.

DETAILED DESCRIPTION OF THE INVENTION

Figure 1:
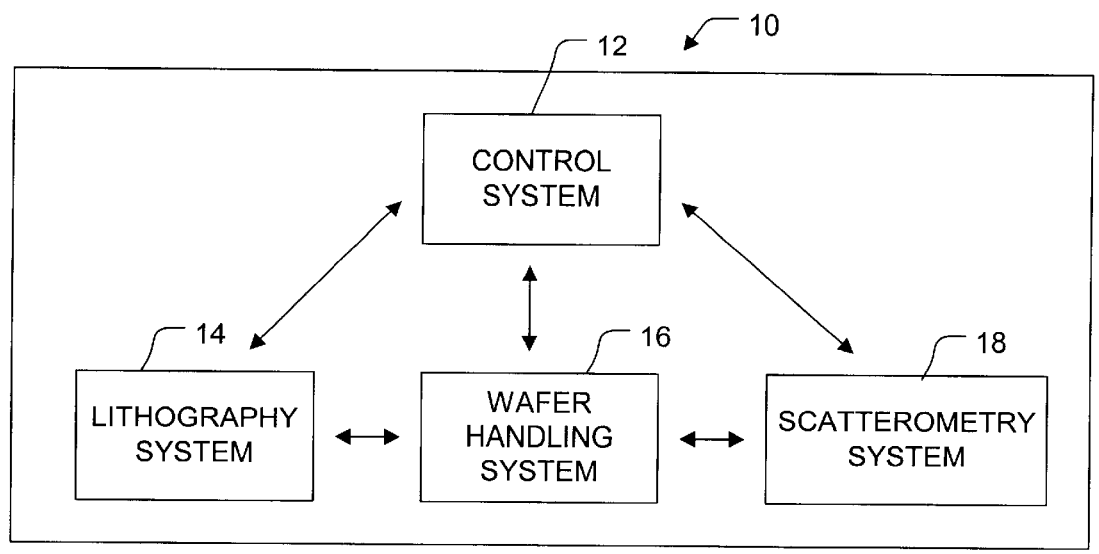
FIG. 1 is a schematic block diagram of a wafer processing system according to one aspect of the present invention.

The present invention will now be described with reference to the drawings. FIG. 1 is a high level schematic block diagram of a wafer processing system 10 according to one aspect of the present invention. The wafer processing system 10 includes a control system 12, a lithography system 14, a wafer handling system 16, and a scatterometry system 18. The lithography system 14, for example, a stepper, provides wafer substrates with a patterned resist that includes a grating that identifies one of a plurality of reticle patterns printed by the lithography system 14 (that is, the grating indicates which reticle was employed for that particular exposure step). The scatterometry system 18 obtains scatterometry measurements from the grating. The control system 12 determines from the scatterometry measurements whether the correct reticle pattern was used by the lithography system 14. If the correct reticle was not used, the control system 12 brings about corrective action, through the wafer handling system 16, for example.

Figure 2:
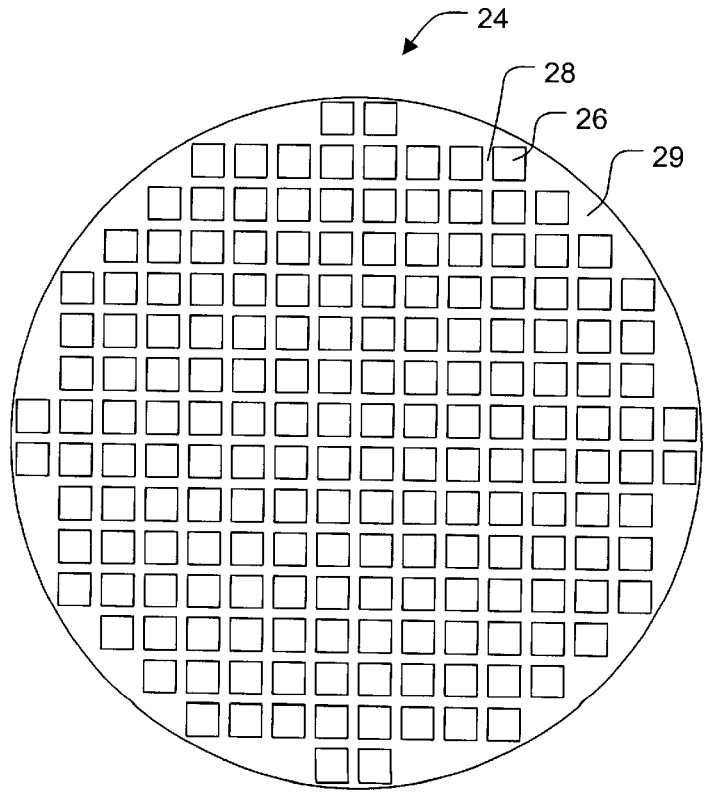
FIG. 2 is a plan view illustration of a wafer.

The grating formed in the resist is generally formed over a nonfunctional portion of the wafer substrate. FIG. 2 illustrates a plan view of an exemplary wafer substrate 24. The wafer substrate 24 includes a plurality of rectangular functional regions 26, wherein devices are formed, and non-functional regions 28, which will be referred to as the score lines 28. The score lines 28 (also known as scribe lines) are located adjacent and between the functional regions 26. The wafer substrate 24 also includes nonfunctional regions 29 around the periphery, as illustrated.

The lithography system 14 prints a reticle pattern and a grating pattern to a resist coated on a wafer substrate.

Printing is the process of transferring a pattern from a reticle to the resist. Printing is generally a repetitive process, wherein a stepper causes selective exposure through the reticle of the resist in each of the functional regions 26, one at a time. The reticle pattern is printed to the functional regions 26 whereas the grating pattern is generally printed to an adjacent nonfunctional region. In one exemplary aspect of the invention, the grating prints in the score lines 28, whereby one or more gratings are formed in the resist within the score lines 28. These gratings may have a pitch, pattern or other type feature characteristic which is unique to the reticle associated therewith, and thus can be employed to identify the reticle pattern printed to the functional regions 26.

Figure 3:
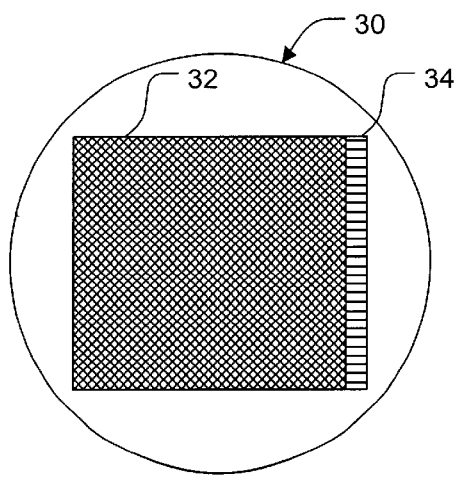
FIG. 3 is a plan view illustration of a reticle according to another aspect of the present invention.

Another aspect of the invention provides a reticle with a grating pattern formed thereon that is adapted to facilitate identification of the reticle through scatterometry measurements taken from a printed grating formed using the reticle. Grating and reticle patterns are defined by portions of the reticle having greater or lesser opacity with respect to a particular type of radiation. FIG. 3 provides an example of a reticle 30 with a substantially rectangular principle portion 32 and an adjacent edge portion 34. The principle portion 32 has a reticle pattern, typically corresponding to a large number of desired structures in a functional region 26 of the wafer substrate 24. The edge portion 34 has a grating pattern corresponding to a desired grating in the score lines 28 of the wafer 24. The grating is unique to the particular reticle and thus is used in identifying the reticle pattern.

Figure 4:
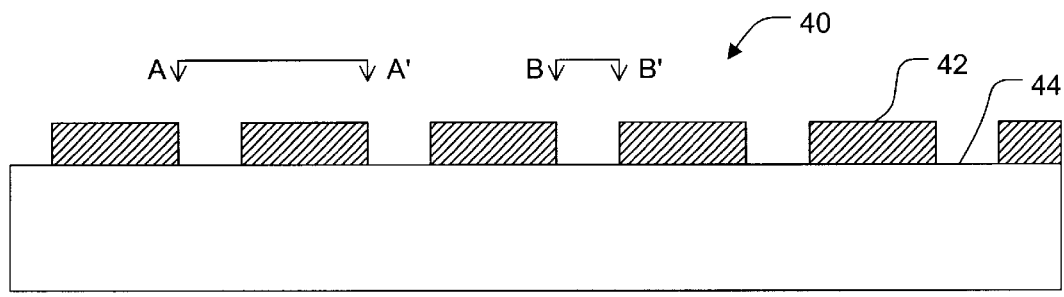
FIG. 4 is an illustration of a grating pattern formed in a resist coating.

FIG. 4 provides an example of a grating 40 formed in a resist 42 on a substrate 44. The grating 40 can be used, with scatterometry, to identify a corresponding reticle pattern. The grating 40 can be characterized, for example, in terms of at least two parameters; one parameter is the pitch of the resist 42 (A to A'), while the other is the gap width (B to B'). A unique grating can be assigned to each of a group of reticle patterns by selecting values for these parameters that vary among the reticles patterns. More complex structures requiring greater numbers of parameters to characterize can also be employed. For example, a family of gratings requiring four parameters to characterize can be obtained by superimposing two gratings of the type of the grating 40. In addition to identifying a reticle pattern, the gratings can be further varied to identify particular reticles or groups of reticles, as may be desired.

Figure 5:
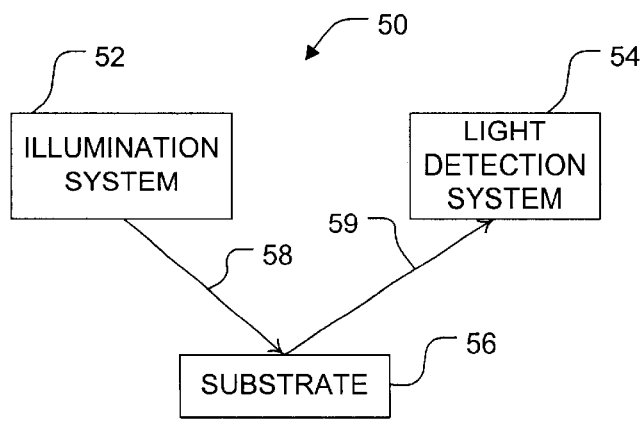
FIG. 5 is a schematic block diagram illustration of a scatterometry system.

The scatterometry system 18 obtains measurements that can be used to identify gratings and corresponding reticle patterns. FIG. 5 illustrates a scatterometry system 50, and includes an illumination system 52 and a light detection system 54. The illumination system 52 provides incident light 58 that scatters from a wafer substrate 56 to produce scattered light 59. The scattered light 59 is detected by the light detection system 54. The light detection system 54 provides data relating to the scattered light 59 to the controller 12.

The illumination system 52 and the light detection system 54 are components of a scatterometer. A scatterometer is a device that measures light scattered from a surface. Scattered light includes light that is reflected and or refracted from a surface, especially light reflected or refracted from a surface with periodic features. For a columnar light source, and where the surface is periodic, such as with a grating, the scattered light is generally diffracted, producing a distinctive intensity distribution. The intensity is distributed with respect to angle of incidence, angle of reflection, wavelength of light, and polarity of light. The intensity distribution depends on a variety of surface characteristics, including composition and geometry.

Several types of scatterometry methodologies are available. The methodologies can be divided according to the portion of the intensity distribution analyzed to obtain information about the surface. One exemplary methodology is 2-Θ scatterometry. Another exemplary methodology is specular spectroscopic scatterometry.

2-Θ scatterometry is based on the intensity distribution of scattered light as a function of angle of incidence. Monochromatic radiation, such as laser light, is generally employed within an illumination system to generate an incident light on the sample surface. The scattered light is distributed into diffracted orders that are located according to the formula:

$$\sin\theta_i + \sin\theta_r = \frac{m\lambda}{d}$$

where $\theta_i$ is the angle of incidence (measured relative to a vector normal to the surface), $\theta_r$ is the angle of reflection, m is the diffraction order, $\lambda$ (lambda) is the wavelength of light, and d is the period of the pattern being evaluated on the surface. The $0^{th}$ diffracted order (m=0) corresponds to specular reflection, that is, scattered light that has an angle of reflection mirroring the angle of incidence. The light intensity for at least one of the diffracted orders is measured. Obtaining light intensity data from several diffracted orders provides more information, but as the grating period, d, becomes small relative to the wavelength, $\lambda$, observing diffracted orders greater than the $0^{th}$ becomes progressively more difficult. In general, observing the light intensity in just one diffracted order, the $0^{th}$ order for example, is sufficient.

Where more data is desired, the intensities of the polar components of the scattered light can be examined separately. In particular, the TM component of scattered light (that with an electric field vibrating parallel to the surface) exhibits one intensity distribution with respect to angle of incidence. The TE component of scattered light (that with an electric field vibrating perpendicular to the surface) exhibits another intensity distribution with respect to angle of incidence. The TE and TM component distributions, taken together, provide more information about the surface than a single distribution that makes no distinctions based on polarity.

Specular spectroscopic scatterometry is based on the intensity distribution of the scattered light as a function of wavelength of incident light. Generally, only one angle of incidence is employed and only the $0^{th}$ diffracted order is considered, although additional data can be obtained using multiple angles of incidence and by examining diffracted orders other than the $0^{th}$. The advantage of using a single angle of incidence and examining only the $0^{th}$ diffracted order is that a single detector at a single position can be employed, thus simplifying the equipment. As with the 2-Θ technique, addition data can be obtained by separately examining the polar components of the scattered light. The light source can be monochromatic with variable wavelength. Alternatively, the light source can be polychromatic while the detection system separately detects the intensities of various wavelengths of light.

The incident light 58 is provided by the illumination system 52, which includes one or more light sources. Depending on the scatterometry technique employed, there can be one light source at a fixed position, one light source with a variable position, or a plurality of light sources with fixed or variable positions. Generally, a single light source is sufficient. The light source can be monochromatic or polychromatic (providing white light, for example). Generally, one or more apertures are used to provide light in a columnar beam. The beam is generally broad enough to simultaneously reflect from ten or more periodic elements, or a number sufficient to produce a clear diffraction pattern.

Light intensities for the scattered light 59 are measured by the light detection system 54, which includes one or more photodetectors, for example. As with the illumination system, depending on the technique involved, there can be one photodetector at a fixed position, one photodetector with a variable position, or a plurality of photodetectors with fixed or variable positions. The photodetectors can be, for example, photo-multipliers or photo-diode arrays. The light detection system 44 can also include one or more polarizing filters to select TE or TM components of the scattered light 52, as may be desired.

For some configurations, the illumination system 52 and the light detection system 54 may be commercially available as part of a scatterometry system. Equipment used for ellipsometry may also be suitable for scatterometry.

Data from the light detection system 54 is provided to the controller 12, which uses the data to determine if the correct reticle pattern was used by the lithography system 14. The controller 12 can include a unit manufactured specifically to control wafer processing, although a general purpose computer system is more commonly employed. Controller 12 generally includes at least a computer system, with suitable hardware and software components.

One function of the controller 12 is to employ data from the light detection system 54 (light intensity data) to identify the unique grating and the corresponding reticle pattern. In principle, with a few simplifying assumptions, the geometry of the grating can be determined directly from the intensity data. However, the mathematics are very difficult and it is generally more practical to create a database of light intensity profiles corresponding to specific gratings and moreover, to the gratings obtained with a specific grating pattern when applied at a specific stage of the manufacturing process. The specific stage of the manufacturing process can affect the scatterometry measurements in that the surface over which the grating is formed often changes in both composition and geometry during the course of a manufacturing process.

A database of light intensity profiles can be generated experimentally or a priori (by calculation). Experimentally, images are taken of the gratings to be identified along with their corresponding reticle patterns. The gratings are general formed on wafers at the same stage in processing at which the reticle pattern in question is applied, thereby taking into account variations in the substrate that can affect the scatterometry measurements. Several gratings may be formed and imaged for each grating patterns to build redundancy into the database and reduce the sensitivity of reticle pattern identification to measurement errors.

A priori approaches can also be employed to build databases of light intensity profiles. Given a description of the surface geometry, the surface composition, and the properties of the component materials, light intensity profiles can be generated by any one of several techniques. In particular, Rigorous Coupled Wave Analysis (RCWA) or the Classical Model Method (CMM) can be employed in generating an a priori database.

After acquiring the light intensity data, the controller 12 searches the database for a match. A match is defined in a statistical sense, such as Partial Least Squares or Minimum Mean Square Error. Several profiles, corresponding to similar surface geometries or multiple measurements of a single grating, may provide a good match to the data and the closest match may be selected. A minimum degree of similarity between the measurement and the closest database entry can be defined. Where the minimum is not met, controller 12 may act under the assumption that the correct reticle pattern was not employed.

When controller 12 identifies that the correct reticle pattern was not employed, it may initiate remedial action. Such action may involve instructions to the wafer handling system 16. The wafer handling system 16 can be any type of automated equipment of the type employed to move wafers about in an integrated circuit device manufacturing process. Remedial action can include, for example, one or more of halting processing of the affected wafers, stripping the resist coating with the incorrect pattern, and applying a new resist coating and repeating the patterning process with a different reticle.

Figure 6:
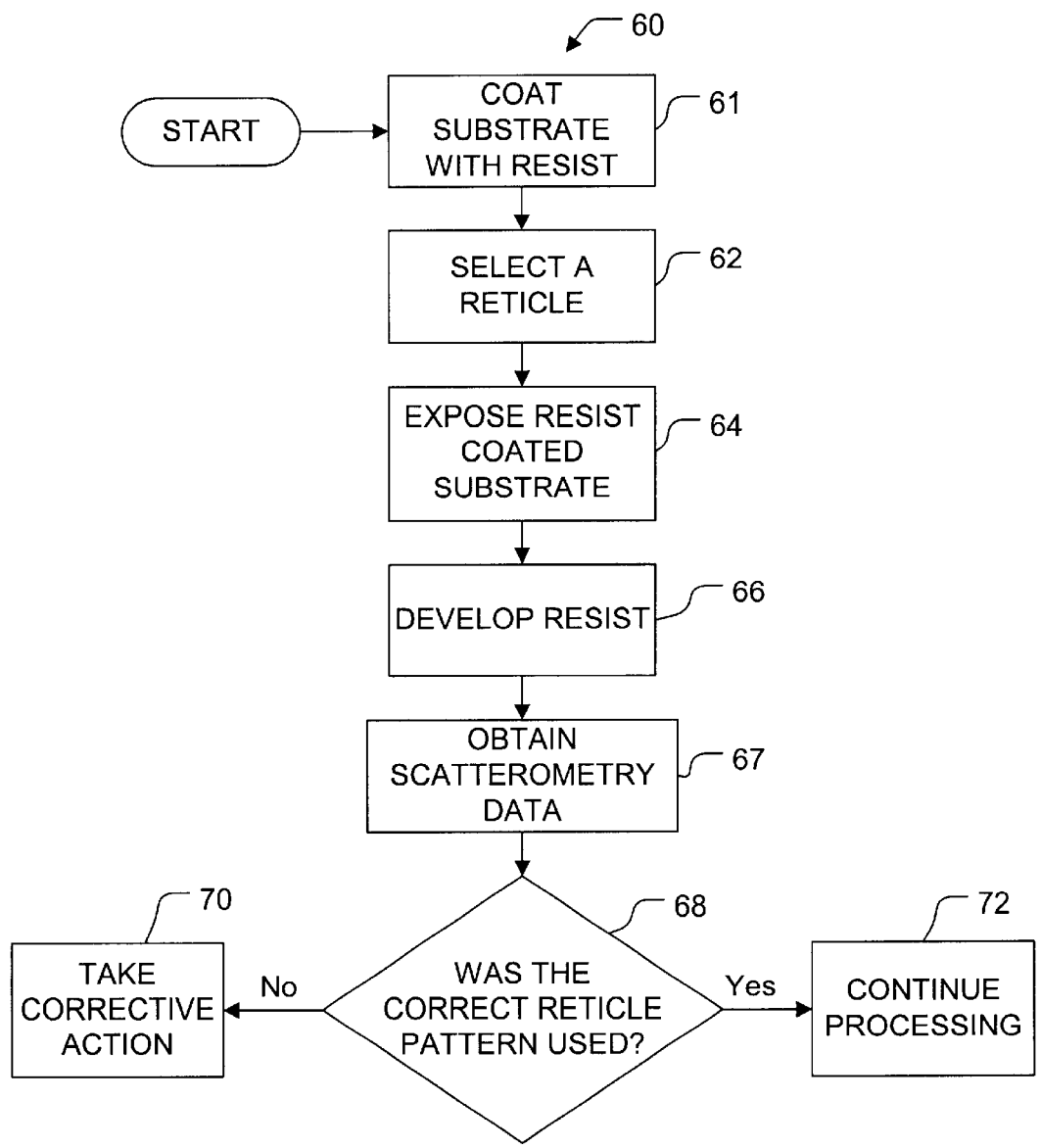
FIG. 6 is a flow diagram of a integrated circuit device manufacturing process according to a further aspect of the present invention.

FIG. 6 is a flow chart of a process 60 according to a further aspect of the present invention. While exemplary method is illustrated and described herein as a series of acts or events, it will be appreciated that the present invention is not limited by the illustrated ordering of such acts or events, as some steps may occur in different orders and/or concurrently with other steps apart from that shown and described herein, in accordance with the invention. In addition, not all illustrated acts or events may be required to implement a methodology in accordance with the present invention. Moreover, it will be appreciated that the methods may be implemented in association with the apparatus and systems illustrated and described herein as well as in association with other systems not illustrated.

Action 61 comprises coating a substrate with a resist, wherein the substrate generally comprises a semiconductor wafer, typically a silicon wafer. Other examples of semiconductors include GaAs and InP. In addition to a semiconducting material, the substrate may include various elements and/or layers; including metal layers, barrier layers, dielectric layers, device structures, active elements and passive elements including silicon gates, word lines, source regions, drain regions, bit lines, bases emitters, collectors, conductive lines, conductive vias, etc.

Action 62, which may take place before or after action 61, comprises selecting a reticle from among a plurality of reticles. Among the plurality of reticles there are a plurality of reticle patterns, only one of which is appropriate for a current step in an integrated circuit device manufacturing process of which process 60 is a portion. The reticles include grating patterns that correspond to the reticle patterns, whereby the reticle patterns can be identified from the grating patterns.

Action 64 comprises exposing the resist to actinic radiation passed through the selected reticle, thereby transferring a reticle pattern and a grating pattern to the resist in terms of more and less soluble portions of the resist. The resist is subsequently developed with action 66. After developing, the resist has been patterned and comprises a grating and a printed reticle pattern.

Action 67 comprises obtaining scafterometry data from the grating, while action 68 includes determining, based on the scatterometry data, whether a reticle with the correct reticle pattern was selected in action 62. If such a reticle was selected, processing continues with action 72; if not, action 70, corrective action, is initiated. The corrective action can involve reprocessing the affected substrates to replace the patterned resist coating with one having the correct pattern by replacing the incorrect reticle with the appropriate one.

Although the invention has been shown and described with respect to certain embodiments, alterations and modifications providing equivalent structures and acts are likely to occur to those of ordinary skill in the art upon the reading and understanding this specification and the associated drawings. Such alterations and modifications are intended to fall within the scope of the present invention, unless expressly stated to the contrary. Components described in functional terms have structure and involve acts, unless otherwise indicated, corresponding to any of the devices and methods known to those of ordinary skill in the art to perform those functions, even though not equivalent to any of the structures and acts that perform those function in the exemplary embodiments of the invention. In addition, while a particular feature of the invention may have been disclosed with respect to only one of several embodiments, such feature may be combined with one or more other features of the other embodiments as may be desired or advantageous for a given or particular application. Furthermore, to the extent that the term "includes" is used in either the detailed description and the claims, such term is intended to be inclusive in a manner similar to the term "comprising."

What is claimed is:

1. An integrated circuit device manufacturing process, comprising:

coating a substrate with a resist;

selecting a reticle from among a plurality of reticles, one or more of which comprises a correct reticle pattern for a current stage in the integrated circuit device manufacturing process, wherein each of the plurality of reticles comprise a reticle pattern and a grating pattern, and wherein each grating pattern uniquely corresponds to and identifies a respective reticle, and wherein the grating patterns are adapted to facilitate identification of the corresponding reticle through scatterometry measurements of gratings formed in the resist from the reticle grating pattern;

selectively exposing the resist to actinic radiation through the selected reticle;

developing the resist to obtain a patterned resist having a reticle pattern portion and a grating pattern portion associated therewith;

obtaining scatterometry data relating to the grating pattern portion of the patterned resist;

determining from the scatterometry data whether the selected reticle comprises the correct reticle of the plurality of reticles for the current stage in the integrated circuit device manufacturing process.

2. The process of claim 1, further comprising undertaking corrective action where it is determined that the selected reticle did not comprise the correct reticle pattern.

3. The process of claim 2, wherein the corrective action comprises stripping the resist, coating the substrate with a new resist, selecting a reticle with the correct reticle pattern, and selectively exposing the new resist to actinic radiation through the reticle with the correct reticle pattern.

4. A wafer processing system, comprising:

a lithography system comprising a plurality of reticles that are printed by the lithography system to obtain patterned resists on wafer substrates, wherein each of the plurality of reticles comprise a reticle pattern and a grating pattern, and wherein each grating pattern uniquely corresponds to and identifies a respective reticle, and wherein the grating patterns are adapted to facilitate identification of the corresponding reticle through scatterometry measurements of gratings formed in the resist from the reticle grating pattern;

a scatterometry system operable to obtain data relating to the patterned resists; and a control system configured to analyze the data to determine whether the lithography system employed a reticle with a pattern appropriate for a particular stage in an integrated circuit device manufacturing process.

5. The wafer processing system of claim 4, where it is determined that the lithography system employed a reticle that did not have the pattern appropriate for the particular stage in the integrated circuit device manufacturing process.

6. The wafer processing system of claim 5, wherein the corrective action comprises stripping the patterned resists from the wafers.

7. The wafer processing system of claim 4, further comprising a wafer handling system configured to replace the reticle in the lithography system with another reticle if the control system determines the reticle employed by the lithography system does not contain the appropriate pattern.

* * * * *

UNITED STATES PATENT AND TRADEMARK OFFICE
CERTIFICATE OF CORRECTION

PATENT NO. : 6,617,087 B1 Page 1 of 1
DATED : September 9, 2003
INVENTOR(S) : Bharath Rangarajan, Bhanwar Singh and Ramkumar Subramanian It is certified that error appears in the above-identified patent and that said Letters Patent is hereby corrected as shown below:

<u>Title page,</u>
Item [75], Inventors, please replace "Ramkumar Subramanian's" city from "San Jose" with -- Sunnyvale --.
Item [*] Notice: please replace the term adjustment days from "0 days" to -- 178 days --.

<u>Column 8,</u>
Line 33, please replace Claim 5 with the following:
9. The wafer processing system of claim 4, wherein the wafer processing system takes corrective action where it is determined that the lithography system employed a reticle that did not have the pattern appropriate for the particular stage in the integrated circuit device manufacturing process.

Signed and Sealed this

Sixteenth Day of December, 2003

JAMES E. ROGAN
*Director of the United States Patent and Trademark Office*